(12) United States Patent
Whitehead et al.

(10) Patent No.: US 10,875,869 B1
(45) Date of Patent: Dec. 29, 2020

(54) DIAZACYCLOBUTENE DERIVATIVES AND METHODS OF SYNTHESIS THEREOF

(71) Applicant: Clemson University, Clemson, SC (US)

(72) Inventors: Daniel C. Whitehead, Clemson, SC (US); James C. Morris, Clemson, SC (US); Chandima J. Narangoda, Clemson, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 16/811,264

(22) Filed: Mar. 6, 2020

Related U.S. Application Data (60) Provisional application No. 62/817,150, filed on Mar. 12, 2019.

(51) Int. Cl.
*C07D 487/04* (2006.01)

(52) U.S. Cl.
CPC ................. *C07D 487/04* (2013.01)

(58) Field of Classification Search
CPC .................................. C07D 487/04
USPC ....................................... 548/951
See application file for complete search history.

(56) References Cited

PUBLICATIONS

Narangoda et al., Accessing the Rare Diazacyclobutene Motif, 2018, Organic Letters, 20, 8009-8013 (Year: 2018).*

* cited by examiner

*Primary Examiner* — Kristin A Vajda

(74) *Attorney, Agent, or Firm* — Joseph T. Guy; Patent Filing Specialist Inc.

(57) ABSTRACT

Provided is a compound having the formula:

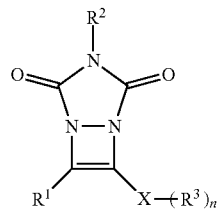

wherein:
$R^1$ is selected from the group consisting of H, aliphatic of 1 to 100 carbons and arene comprising up to 100 carbons;
$R^2$ is selected from the group consisting of H, aliphatic of 1 to 100 carbons and arene comprising up to 100 carbons;
each $R^3$ is independently selected from the group consisting of H, aliphatic of 1 to 100 carbons and arene comprising up to 100 carbons;
X is selected from the group consisting of B, O, N, S, Se and P; and
n is 1-4 as necessary to complete the valence of X formed by the reaction of a compound of Formula III:

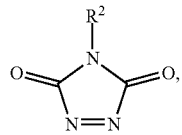

Formula III and a compound of Formula IV:

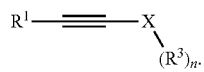

Formula IV

63 Claims, 5 Drawing Sheets

Compound 19　　　　Compound 20　　Compound 21

Compound 22　　Compound 23　　Compound 24　　Compound 25

Compound 26　　Compound 27　　　　　　　　FIG. 4B

Compound 28

DIAZACYCLOBUTENE DERIVATIVES AND METHODS OF SYNTHESIS THEREOF

CROSS-REFERENCE TO RELATED APPLICATIONS

The application claims priority to U.S. Patent Appl. No. 62/817,150 filed Mar. 12, 2019 which is incorporated herein by reference.

FIELD OF THE INVENTION

The present invention is related to compounds of Formula I:

Formula I with a particularly preferred embodiment represented by Formula II:

Formula II and the synthesis thereof wherein $R^1$, $R^2$, $R^3$, Y, X and n are defined further herein.

BACKGROUND

Diazacyclobutenes are a unique class of four membered heterocycles consisting of a carbon-carbon double bond and two adjacent nitrogen atoms. Diazacyclobutenes have long been sought for their expected utility in synthesis and for exploration of their reactivity. The availability of diazacyclobutenes has been limited by their difficult synthetic path and therefore only a few have been available for study.

Historically, these heterocycles gained attention in the literature owing to the electronic framework resident in the moiety that formally follows the Hückel (4n+2) rule of aromaticity. Thus, these molecules, their potential aromaticity, and their putative reactivity have been of theoretical interest but their availability has limited evaluation and exploitation of their potential.

Through diligent research a novel synthetic approach has been developed which makes a large class of diazacyclobutenes available for further research into their viability as synthetic tools and of their potential reactivity and functionality in a variety of systems. The novel synthetic procedure and novel diazacyclobutenes made available by the synthetic procedure are provided herein.

SUMMARY OF THE INVENTION

The invention is related to a novel synthetic procedure for diazacyclobutenes and novel diazacyclobutenes provided thereby.

A particular advantage is the ability to provide a novel class of diazacyclobutenes for evaluation as a synthetic tool or for reactivity in a variety of systems.

These and other embodiments, as will be realized, are provided in a compound having the formula:

wherein:

$R^1$ is selected from the group consisting of H, aliphatic of 1 to 100 carbons and arene comprising up to 100 carbons;

each $R^3$ is independently selected from the group consisting of H, aliphatic of 1 to 100 carbons and arene comprising up to 100 carbons;

Y represents those elements necessary to form a 5 or 6 membered ring;

X is selected from the group consisting of B, O, N, S, Se and P; and n is 1-4 as necessary to complete the valence of X.

Yet another embodiment is provided by compound having the formula:

wherein:

$R^1$ is selected from the group consisting of H, aliphatic of 1 to 100 carbons and arene comprising up to 100 carbons;

$R^2$ is selected from the group consisting of H, aliphatic of 1 to 100 carbons and arene comprising up to 100 carbons;

each $R^3$ is independently selected from the group consisting of H, aliphatic of 1 to 100 carbons and arene comprising up to 100 carbons;

X is selected from the group consisting of B, O, N, S, Se and P; and n is 1-4 as necessary to complete the valence of X.

Yet another embodiment is provided in a method for forming a diazacyclobutene derivative comprising the steps of:

forming a first solution comprising a solvent and a compound of Formula III:

Formula III wherein:
R² is selected from the group consisting of H, aliphatic of 1 to 100 carbons and arene comprising up to 100 carbons;
forming a second solution comprising a second solvent and a compound of Formula IV:

Formula IV wherein:
R¹ is selected from the group consisting of H, aliphatic of 1 to 100 carbons and arene comprising up to 100 carbons;
each R³ is independently selected from the group consisting of H, aliphatic of 1 to 100 carbons and arene comprising up to 100 carbons;
X is selected from the group consisting of B, O, N, S, Se and P; and
n is 1-4 as necessary to complete the valence of X;
mixing the first solution and said second solution to form a reaction solution; and
heating the reaction solution to a reaction temperature.

Yet another embodiment is provided a method for forming a diazacyclobutene derivative comprising the steps of:
forming a first solution comprising a solvent and a compound having Formula V:

Formula V wherein:
Y represents those elements necessary to form a 5 or 6 membered ring;
forming a second solution comprising a second solvent and a compound of Formula IV:

Formula IV wherein:
R¹ is selected from the group consisting of H, aliphatic of 1 to 100 carbons and arene comprising up to 100 carbons;
each R³ is independently selected from the group consisting of H, aliphatic of 1 to 100 carbons and arene comprising up to 100 carbons;
X is selected from the group consisting of B, O, N, S, Se and P; and
n is 1-4 as necessary to complete the valence of X;
mixing the first solution and the second solution to form a reaction solution; and
heating the reaction solution to a reaction temperature.

DESCRIPTION

The present invention is related to diazacyclobutene derivatives and their method of synthesis.

The present invention provides a straightforward approach for the synthesis of rare diazacyclobutanes by means of a formal [2+2] cycloaddition between preferably alkynyl sulfides or selenides and 4-phenyl-1,2,4-triazoline-3,5-dione (PTAD). This effort provides ready access to a molecular scaffold that was hitherto inaccessible, with the exception of a handful of examples. Experimental and computational evidence suggests that the compounds are not aromatic, despite formally obeying the Hückel 4n+2 rule for aromaticity.

Figure 4A:
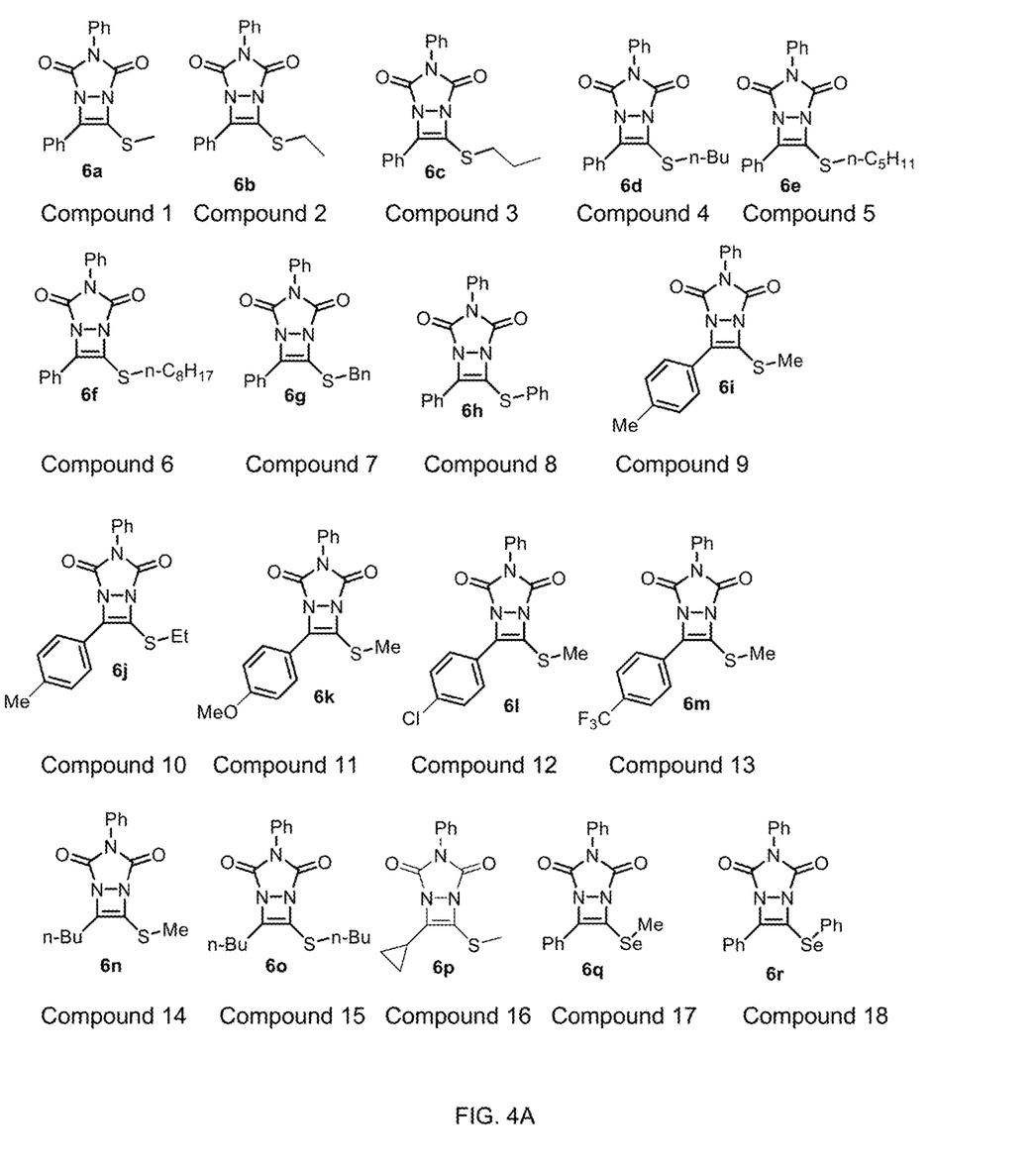
FIGS. 4A and 4B comprise schematic structures of various embodiments of the invention.
Figure 4B:
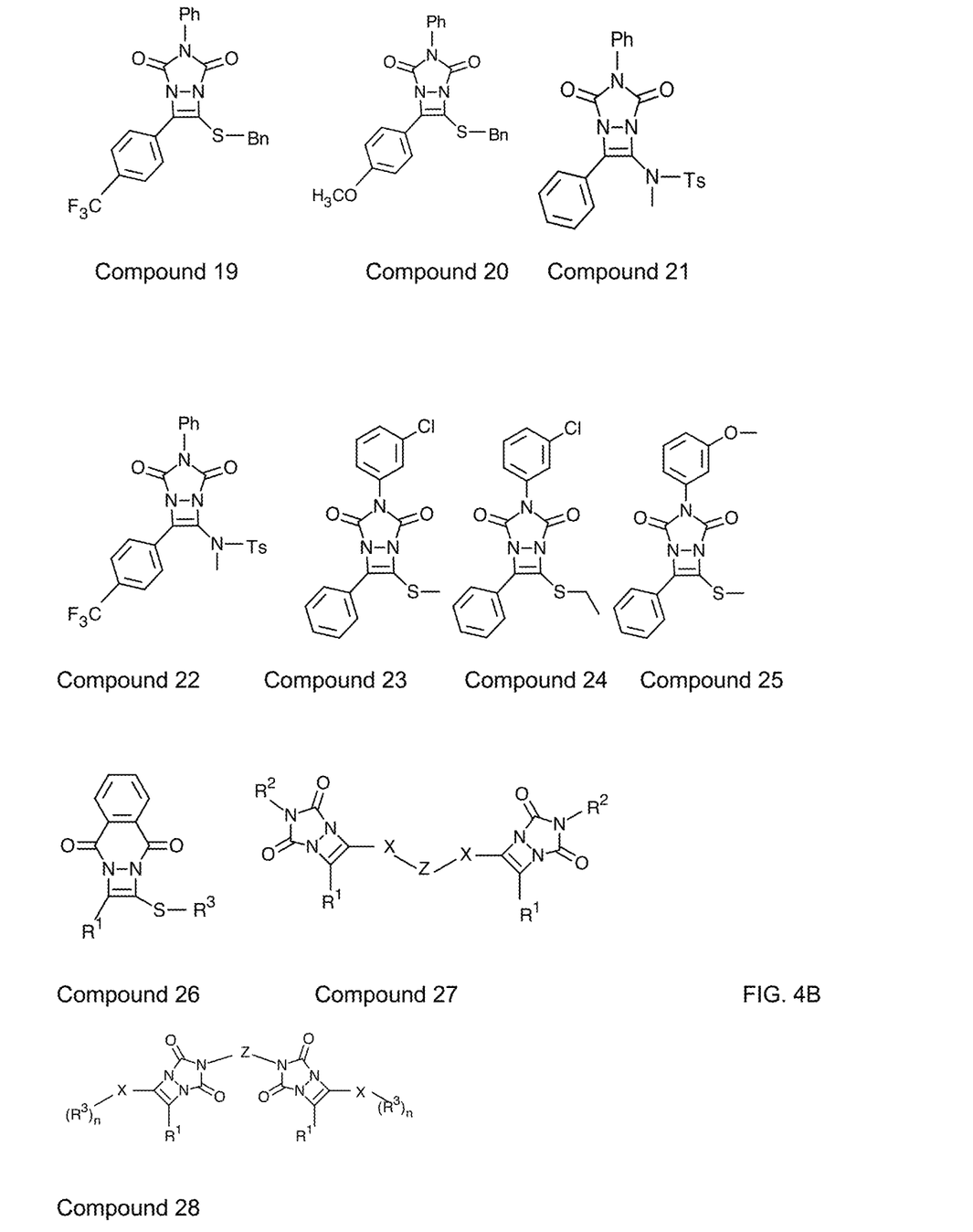

Diazacyclobutene derivatives can be prepared by the reaction of selected compounds of Formula V:

Formula V with the reaction being described using an exemplary embodiment 1,2,4-triazoline-3,5-diones of Formula III:

Formula III with alkynyl species of Formula IV:

Formula IV wherein R¹, R², R³, Y, n and X are described elsewhere herein, to form a derivative of diazacyclobutene of Formula I represented for the purposes of discussion by the exemplary embodiment thereof as Formula II without limit thereto. Exemplary compounds of Formula I:

Formula I are illustrated schematically in FIGS. 4A and 4B.

The reaction of the compound of exemplary Formula III and the compound of Formula IV is preferably done in dry glassware, such as flame dried. The compound of Formula III and the compound of Formula IV are added and allowed to react, preferably at above a reaction temperature and more preferably at reflux temperature of the solvent for a sufficient time to allow for complete reaction. The reaction temperature is preferably at least −20° C. to no more than 300° C. A temperature of 50° C. to 250° C. is suitable for demonstration of the invention with about 100° C. to 200° C. being preferred. The reaction time required is dependent on temperature with at least about 6 hours to no more than about 24 hours being preferred. Below about 6 hours yields can be compromised and above about 24 hours is unnecessary in most embodiments. The reaction product is obtained by removing solvent, preferably under reduced pressure, with purification. While not limited thereto, flash chromatography is a particularly suitable purification method for demonstration of the invention. Flash chromatography accomplished with hexane and ethyl acetate in a gradient from 100% hexane to 80:20 hexane/ethyl acetate is suitable for demonstration of the invention. It is preferable that the compound of Formula III be dissolved in a suitable solvent with dropwise addition of the compound of Formula IV in a solvent, and preferably the same solvent as Formula III, for convenience. In an alternate embodiment catalyzing the reaction of Formula III and Formula IV with a Lewis Acid catalyst, such as, but not limited to, silver (I) triflate is advantageous. The Lewis Acid catalyst is particularly preferred when X is a nitrogen.

In the formulas, $R^1$ and $R^2$ are independently selected from the group consisting of H, aliphatic of 1 to 100 carbons and arene comprising up to 100 carbons or combinations thereof. The aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile or an organometallic. $R^1$ or $R^2$ independently are preferably selected from the group consisting of aliphatic of 1-10 carbons more preferably 1-5 carbons, arene of up to 20 carbons more preferably no more than 6 carbons, substituted aliphatic of 1-10 carbons more preferably 1-5 carbons or substituted arene of up to 20 carbons and more preferably no more than 6 carbons. The preferred substituents are selected from the group consisting of halogen, hydroxyl, carboxyl, and amine. Preferably at least one of $R^1$ or $R^2$ comprises a phenyl group.

In the formulas, X is selected from the group consisting of B, O, N, S, Se and P with S and Se, being preferred.

In the formulas, n is 1-4 as necessary to complete the valence of X. When n is more than 1 each $R^3$ can be the same or defined independently. It is preferred that n is 1 or 2.

In the formula, Y represents those elements necessary to form a 5 or 6 member ring preferably selected from the group consisting of C, N, O and combinations thereof wherein Y may be substituted. Particularly preferred are —$(CR^4{}_A)_m$—, —$NR^2$— or —O— wherein m is an integer selected from 1 and 2, A is an integer of 1 or 2, $R^2$ is defined elsewhere herein and each $R^4$ is independently selected from the group consisting of H, aliphatic of 1 to 100 carbons and arene comprising up to 100 carbons or combinations thereof. The aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile or an organometallic. When m is 2, independent $R^4$ groups may be taken together to form an organic ring, a heteroatom ring or an arene. In a particularly preferred embodiment m is 2 and independent $R^4$ groups are taken together to form a phenyl ring.

In the formulas, $R^3$ is independently selected from the group consisting of H, aliphatic of 1 to 100 carbons and arene comprising up to 100 carbons or combinations thereof. The aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile or an organometallic. $R^3$ independently are preferably selected from the group consisting of aliphatic of 1-10 carbons more preferably 1-5 carbons, arene of up to 20 carbons more preferably no more than 6 carbons, substituted aliphatic of 1-10 carbons more preferably 1-5 carbons or substituted arene of up to 20 carbons and more preferably no more than 6 carbons. The preferred substituents are selected from the group consisting of arene, halogen, hydroxyl, carboxyl, and amine. $R^3$ preferably comprise a group selected from a phenyl group, an alkyl of 1-8 or a benzyl group.

In one embodiment Formula IV is an alkynyl sulfide. Alkynyl sulfides are accessible by direct deprotonation of terminal alkynes. The deprotonation is followed by interception with elemental sulfur followed by quenching the incipient sulfide anion with an aliphatic halide. In an alternate embodiment deprotonation is followed by direct reaction of the lithium acetylide intermediate with an appropriate dialkyl disulfide.

In an embodiment of the invention dimers or oligomers may be formed, preferably, at $R^1$, $R^2$, $R^3$ or $R^4$ as illustrated in FIG. 4B as exemplified by compounds 27 and 28 with the understanding that any of $R^1$, $R^2$, $R^3$ or $R^4$ could be substituted with Z. In compounds 27 and 28 $R^1$, $R^2$, $R^3$, X and n are defined elsewhere herein. In compounds 27 and 28 Z is a linking group and preferably an aliphatic, oligomeric glycol, or arene linking group with alkyl of 1 to 10 carbons being a preferred linking group. Compounds 27 and 28 are exemplary of similar linked compounds based on Formula I.

In a particularly preferred embodiment the compound of Formula I can be prepared in a single pot at room temperature thereby eliminating the necessity of isolating Formula III or relying on expensive Formula III as a raw material. The synthesis, represented schematically as:

One-pot protocol:

Room Temperature
No need to isolate TAD derivative will be described utilizing phenylurazole as an exemplary embodiment without limit thereto. The urazole, such as phenylurazole, is treated with calcium hypochlorite in dichloromethane (DCM) in the presence of sodium sulfate, preferably anhydrous, to form a compound of Formula III represented herein with $R^2$ being phenyl. The reaction is preferably carried out at ambient or room temperature (RT) until complete such as about 2 hours. Magnesium chloride, or a similar reactant, is preferable added to neutralize reaction products formed during the formation of the compound of Formula III. The compound of Formula III, which is essentially in-situ, is further reacted with a compound of Formula IV, as discussed elsewhere herein, to form the compound of Formula I.

The solvent is not particularly limited, however, tetrahydrofuran (THF), acetonitrile (ACN), dichloromethane (DCM), toluene, lower alkyl alcohols such as methanol and ethanol, dialkyl ethers such as diethyl ether and chloroform have been demonstrated to be suitable for demonstration of the invention.

Throughout the specification the term aliphatic refers to a moiety of an alkyl, alkenyl or alkynyl and is intended to refer to a substituted or unsubstituted group which may be linear, branched or cyclic including those cyclic rings comprising a heteroatom as a substitute for a carbon in the ring unless otherwise specified.

Throughout the specification the term arene is intended to refer a moiety of a hydrocarbon arene moiety, also referred to in the art as an aryl, or a moiety of a heteroatom arene either of which may be substituted or unsubstituted. Included are fused arene groups unless otherwise specified. Particularly preferred arenes are aryls, oxygen containing arenes, nitrogen containing arenes and the like.

Throughout the description a range of subscripts, such as 1-10, is intended to be inclusive of all intervening integers. For example, 1-5 represents 1, 2, 3, 4 or 5 or any range there between such as 2-4.

EXAMPLES

Experimental Details

All reagents were purchased from commercial sources and used without purification. THF and acetonitrile were dried prior to use over sodium/benzophenone and phosphorous pentoxide, respectively. $^1H$ and $^{13}C$ nuclear magnetic resonance (NMR) spectra were collected on Bruker Avance 300 MHz, 500 MHz and JOEL Eclipse 500 MHz NMR spectrometers using $CDCl_3$. Chemical shifts are reported in parts per million (ppm). Spectra are referenced to residual solvent peaks. Infrared spectroscopy data were collected using a Shimadzu IRAffinity-1S instrument (with MIRacle 10 single reflection ATR accessory) operating over the range of 400 to 4000 $cm^{-1}$. Flash silica gel (40-63 μm) was used for column chromatography. All known compounds were characterized by $^1H$ and $^{13}C$ NMR and are in complete agreement with samples reported elsewhere. All new compounds were characterized by $^1H$ and $^{13}C$ NMR, attenuated total reflectance Fourier transform infrared (ATR-FTIR), high resolution mass spectroscopy (HRMS), x-ray diffraction (XRD), and melting point (where appropriate).

Synthesis of Alkynyl Sulfides

In one method the alkynyl sulfide was prepared by adding a solution of the terminal alkyne (1 equiv) in THF (5 mL for 1 mmol of alkyne) under argon atmosphere to a flame dried 2-neck round bottom flask with stirring. A septum was placed over the round bottom inlets and the solution was cooled to about −78° C. A solution of n-BuLi (1.1 equiv, 1.6 M in hexane) was added. The reaction solution was stirred for 30 minutes followed by the addition of 1 molar equivalent of finely ground sulfur powder by briefly removing one of the septa and then replacing it. The resulting mixture was stirred for 1 hour at about −78° C. The resulting mixture was allowed to gradually warm to 0° C. until the sulfur was completely consumed, thus producing a red colored lithium alkynyl thiolate. The corresponding alkyl halide (5.0 mmol, 1 equiv) was then added in a dropwise fashion. After 4 h the reaction mixture was quenched with saturated aqueous $NH_4Cl$ (5 mL for 1 mmol of alkyne). The reaction mixture was then poured into a separatory funnel, and the aqueous layer was extracted with diethyl ether (3×5 mL for 1 mmol of alkyne). The combined ether extracts were washed with saturated aqueous brine (5 mL for 1 mmol of alkyne). The organic layer was then dried over $Na_2SO_4$, decanted, and the solvent was evaporated by rotary evaporation. The crude residue was then purified by flash chromatography (silica gel, hexane) to afford the desired alkynyl sulfide. The alkynyl sulfide used for the synthesis of Compounds 3-7 were synthesized using this protocol.

In a second method alkynyl sulfides were prepared by adding a solution of the terminal alkyne (1 equiv) dissolved in THF (1 mL for 1 mmol of alkyne) to a flame dried round bottom flask, equipped with a magnetic stir bar and a septum. The solution was then cooled to −78° C. and n-BuLi (1.1 equiv, 1.6 M in hexane) was added dropwise. This solution was stirred for 10 min after which an appropriate dialkyl disulfide (1.2 equiv) was added at −78° C. The solution was then allowed to warm to room temperature and stirred for 1 hour. The reaction mixture was quenched with saturated aqueous $NH_4Cl$ (5 mL for 1 mmol of alkyne) and extracted with ethyl acetate (3×5 mL for 1 mmol of alkyne). The combined organic layers were dried over $Na_2SO_4$, decanted, and concentrated by rotary evaporation. The crude mixture was purified by flash chromatography (silica gel, hexanes) to yield the desired alkynyl sulfide.

The corresponding alkynyl selenide analogs for the synthesis of 1,2-diazacyclobutenes for compounds 17 and 18 were synthesized using similar conditions as above.

General Synthesis of Diazacyclobutenes

To a flame dried round bottom flask equipped with a stir bar was added a solution of 4-phenyl-1,2,4-triazoline-3,5-dione (PTAD) (1 equiv) in dry acetonitrile (5 mL for 1 mmol of PTAD). To this stirring solution was added dropwise a solution of alkynyl sulfide or alkynyl selenide (1.3 equiv) in dry acetonitrile (5 mL for 1.3 mmol of alkynyl substrate). Then the round bottom flask was attached to a water cooled condenser and the mixture was refluxed for 24 h. The resultant mixture was concentrated under reduced pressure and purified via flash chromatography with hexane and ethyl acetate (gradient from 100% hexane to 80:20 hexane/ethyl acetate) to afford the corresponding diazacyclobutene.

Example 1: Synthesis of Compound 1

The yield for the formation of Compound 1 in a series of common solvents was determined by reacting PTAD (1 equiv.) and $C_6H_5$-CC-$SCH_3$ (1.3 equiv) in a series of common solvents. The mixtures were heated under reflux conditions for 24 hours. The results are reported in Table 1. Acetonitrile was found to afford the highest yield of 89% yield as indicated for Sample 5 even though the reaction tolerates a range of solvents reasonably well. Chloroform and dichloromethane resulted in slightly lower yields of 82% and 78%, respectively, whereas tetrahydrofuran and toluene provided even lower yields of 68% and 67% as evidenced by samples 1-4. Reaction conditions were further studied by conducting a time study by refluxing in acetonitrile for 6 hours (80%) and 12 hours (83%) resulting in good but slightly lower yields compared to the corresponding 24 hour reaction as evidenced by Samples 6-7. Furthermore, decreasing the equivalence of the alkynyl sulfide of Formula IV resulted in lower isolated yields of product resulting in yields of 71%, 69%, and 72% for 1.0, 1.1, and 1.2 equiv of Formula IV respectively, as evidenced in Samples 8-10. When the concentration of the reaction was doubled (i.e. to 0.2 M in PTAD), the yield was also diminished to 75%. Based on these observations the conditions used for Sample 5 were used for subsequent experiments.

TABLE 1

| Sample | Solvent | Molar Equivalents | time (H) | Yield (%) |
| --- | --- | --- | --- | --- |
| 1 | $CHCl_3$ | 1.3 | 24 | 82 |
| 2 | DCM | 1.3 | 24 | 78 |
| 3 | THF | 1.3 | 24 | 68 |
| 4 | Toluene | 1.3 | 24 | 67 |
| 5 | ACN | 1.3 | 24 | 89 |
| 6 | ACN | 1.3 | 6 | 80 |
| 7 | ACN | 1.3 | 12 | 83 |
| 8 | ACN | 1.0 | 24 | 71 |
| 9 | ACN | 1.1 | 24 | 69 |
| 10 | ACN | 1.2 | 24 | 72 |
| 11 | ACN | 1.3 | 24 | 75 |

In Table 1 Molar Equivalents is the moles of Formula IV per mole of Formula III, DCM is dichloromethane, THF is tetrahydrofuran, ACN is acetonitrile, yield is based on isolated material after column chromatography.

Example 2: Synthesis of Compounds 1-22

A series of diazacyclobutenes were prepared using PTAD as the reactant of Formula III wherein $R^2$ is phenyl. Varying the length of the alkyl chain resident on the sulfur atom, $R^2$, of the alkynyl sulfide component were prepared as Compounds 1-6. Products bearing shorter n-alkyl chains at $R^2$ such as methyl, ethyl, n-propyl, and n-butyl were successfully converted into their corresponding diazacyclobutene derivatives, Compounds 1-4, in 77-89% yields. The diazacyclobutene derivatives bearing n-pentyl and n-octyl groups at sulfur, Compounds 5 and 6, were generated in 78% and 81% yields, respectively. Incorporating a benzyl group at $R^2$, Compound 7, resulted in a moderate yield of 62%. The $R^3$=Ph analog, Compound 8, was prepared in 85% isolated yield at 1 mmol scale. The results are provided in Table 2:

TABLE 2

| Compound | $R^1$ | X | $R^3$ | Yield(%) |
| --- | --- | --- | --- | --- |
| 1 | —$C_6H_5$ | S | —$CH_3$ | 89 |
| 2 | —$C_6H_5$ | S | —$CH_2CH_3$ | 84 |
| 3 | —$C_6H_5$ | S | —$(CH_2)_2CH_3$ | 80 |
| 4 | —$C_6H_5$ | S | —$(CH_2)_3CH_3$ | 77 |
| 5 | —$C_6H_5$ | S | —$(CH_2)_4CH_3$ | 78 |
| 6 | —$C_6H_5$ | S | —$(CH_2)_7CH_3$ | 81 |
| 7 | —$C_6H_5$ | S | —$(CH_2)C_6H_5$ | 62 |
| 8 | —$C_6H_5$ | S | —$C_6H_5$ | 81 |
| 9 | —$C_6H_4CH_3$ | S | —$CH_3$ | 92 |
| 10 | —$C_6H_4CH_3$ | S | —$CH_2CH_3$ | 77 |
| 11 | —$C_6H_4OCH_3$ | S | —$CH_3$ | 74 |
| 12 | —$C_6H_4Cl$ | S | —$CH_3$ | 85 |
| 13 | —$C_6H_4CF_3$ | S | —$CH_3$ | 83 |
| 14 | —$(CH_2)_3CH_3$ | S | —$CH_3$ | 61 |
| 15 | —$(CH_2)_3CH_3$ | S | —$(CH_2)_3CH_3$ | 56 |
| 16 | (cyclopropyl) | S | —$CH_3$ | 94 |
| 17 | —$C_6H_5$ | Se | —$CH_3$ | 80 |
| 18 | —$C_6H_5$ | Se | —$C_6H_5$ | 93 |
| 19 | —$C_6H_4CF_3$ | S | —$(CH_2)C_6H_5$ | 68 |
| 20 | —$C_6H_4OCH_3$ | S | —$(CH_2)C_6H_5$ | 89 |
| 21 | —$C_6H_5$ | N | —$CH_3$ and Ts | 27 |
| 22 | —$C_6H_4CF_3$ | N | —$CH_3$ and Ts | 40 | wherein Ts is tosylate.

Example 3: Synthesis of Compounds 23-25

A series of diazacyclobutenes were prepared using PTAD as the reactant of Formula II wherein R1, $R^2$ and $R^3$ are is indicated in Table 3:

TABLE 3

| Compound | $R^1$ | $R^2$ | X | $R^3$ | Yield(%) |
| --- | --- | --- | --- | --- | --- |
| 23 | —$C_6H_5$ | -m-$C_6H_4Cl$ | S | —$CH_3$ | 30 |
| 24 | —$C_6H_5$ | -m-$C_6H_4Cl$ | S | —$CH_2CH_3$ | 29 |
| 25 | —$C_6H_5$ | -m-$C_6H_4OCH_3$ | S | —$CH_3$ | 30 |

The reactivity of alkyl phenylacetylene sulfides bearing para-substituted electron donating and withdrawing substituents on the phenyl group situated at $R^1$ was evaluated. Substrates with arenes bearing electron donating groups such as p-methyl, represented by Compounds 9 and 10, and p-methoxy, represented by Compound 11, proceeded with good yield. Substrates with arenes bearing electron withdrawing substituents such as p-chloro, Compound 12, and p-trifluoromethyl, Compound 13, also generated the corresponding diazacyclobutene derivatives in good yields. Thioacetylenes bearing an alkyl chain at $R^1$ in lieu of an arene were evaluated. Compounds 14 and 15 were prepared in moderate yields of 61% and 56%, respectively. Additionally, Compound 16, where $R^1$=cyclopropyl, was prepared in 94% yield. The use of selenium as the chalcogen, as opposed to sulfur, provided 80 and 93% yield, as indicated for Compounds 17 and 18, respectively. The reaction also scales reasonably well. The synthesis of Compound 8 was carried out on a 6 mmol scale, returning the diazacyclobutene in 81% isolated yield (1.87 g).

The compounds prepared are almost universally crystalline allowing for confirmation of the structure by single crystal x-ray diffraction for many of the samples. Analysis indicated that the core diazacyclobutene scaffold formally obeys the Hückel 4n+2 rule for aromaticity, and a number of computational studies have explored the potential for aromaticity in this system. All of the compounds analyzed by X-ray crystallography show a puckered structure with the five-membered ring canted out-of-plane with respect to the core diazacyclobutene moiety. On average, the angle of intersection of the four-membered and five-membered ring planes is $\theta=125.0\pm1.8°$.

Figure 1:
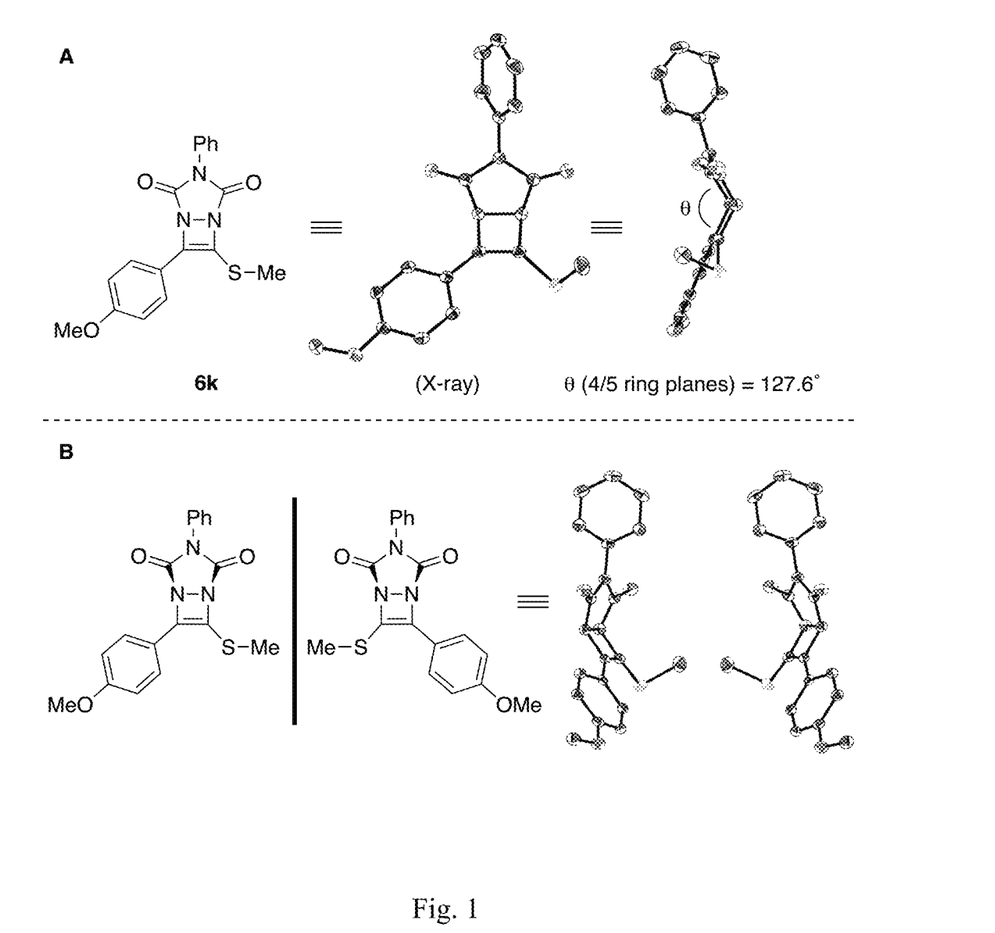
FIG. 1 is a pictorial representation of a single crystal x-ray diffraction analysis of an embodiment of the invention.
Figure 2:
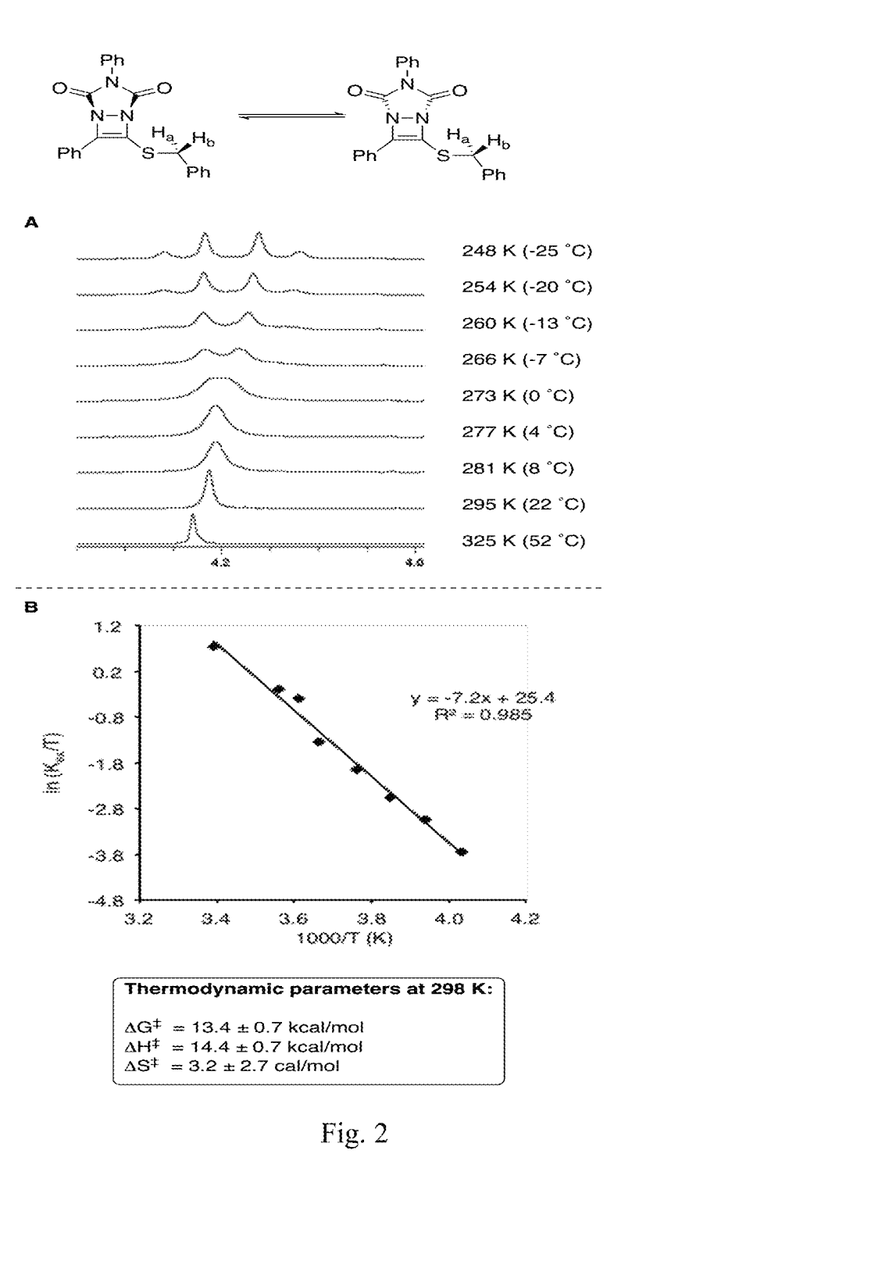
FIG. 2 is a graphical representation of a dynamic NMR analysis of an embodiment of the invention.

Single crystal X-ray structures of diazacyclobutene of Compound 9 are illustrated in FIG. 1 and dynamic NMR analysis (300 MHz) of the inversion barrier a representative compound is illustrated in FIG. 1. The puckered geometry of the 4/5 bicyclic ring system results in the appearance of two distinct enantiomers as illustrated in FIG. 1B in the unit cell for compound evaluated by X-ray analysis. These two enantiomers appear to rapidly equilibrate at room temperature. Thus, double nitrogen inversion barrier was analyzed by dynamic $^1$H NMR analysis under cryogenic conditions. Specifically, the S-benzyl methylene protons in diazacyclobutene, Compound 7, appear as a clean singlet (4.21 ppm, 300 MHz) at room temperature, but gradual cooling of the sample to $-25°$ C. revealed a clear coalescence point followed by resolution into a clean AB quartet (4.22 ppm, 4.15 ppm, J=12.8 Hz), indicative of diastereotopicity at lower temperatures as illustrated graphically in FIG. 2A. Dynamic NMR simulations and line shape analyses were performed using Bruker Topspin version 3.5 software, and the exchange rate constant, $K_{ex}$, was extracted. An Eyring plot, presented graphically in FIG. 2B, was used to calculate the $\Delta H^\dagger$ and $\Delta S^\dagger$ terms: 14.4±0.7 kcal/mol and 3.2±2.7 cal/mol·K, respectively. From these data, the activation energy, ($\Delta G^\dagger$), for the inversion was determined to be 13.4±0.7 kcal/mol at 298 K (25° C.). A similar analysis was conducted for the S-ethyl methylene protons, Compound 2 revealing an inversion barrier, $\Delta G^\dagger$, of 13.6±0.5 kcal/mol at 298K (25° C.).

Figure 3:
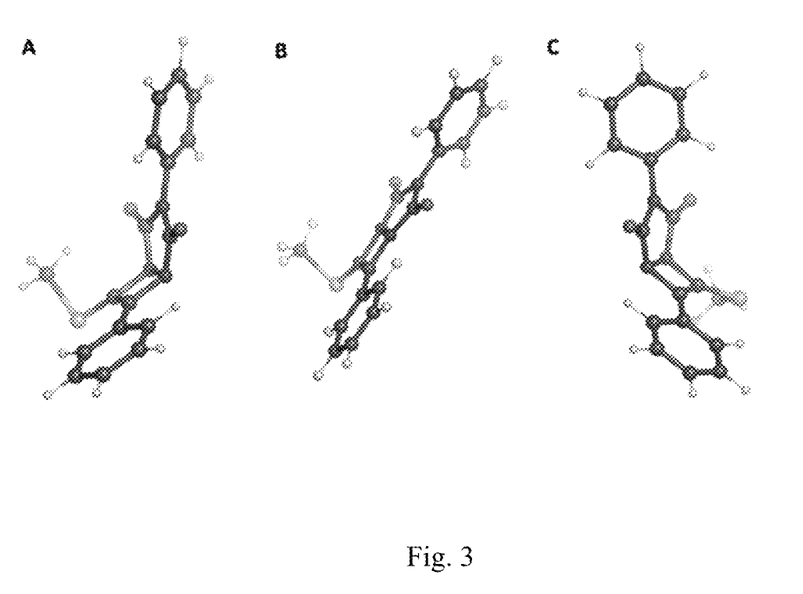
FIG. 3 is a pictorial representation of calculated (DFT) energy minima (A and C) and the planar transition state (Structure B) of the ring inversion.

The inversion barrier was determined computationally for Compound 1 at 25° C. in the gas phase and in simulated chloroform solvent, using the wB97X-D/6-311+G(2df,2pd) DFT method and the SMD solvation model of Cramer et al. as implemented in the Gaussian 16 program suite. The results, $\Delta H^\dagger$=12.6 and 11.3 kcal/mol respectively, show solvation lowering the enthalpy barrier to inversion which accords with the larger dipole moment (2.62 vs 2.25 D) calculated for the near-planar transition structure (TS) for inversion than for the strongly bent ground state (GS) minima. To further explore this issue TS and GS structures were analyzed using the wavefunction-based T1 method of Hehre, et al., with solvation computed at the B3LYP/6-31+G*/SM8 level, as implemented in the Spartan quantum chemistry code as illustrated in FIG. 3. FIG. 3 illustrates the calculated minima (A and C) and transition state (B) for the double nitrogen inversion of Compound 1 calculated at the wB97X-D/6-311+G(2df,2pd) level. The resulting gas, and CHCl$_3$, solvated barriers were 14.9 and 14.2 kcal/mol respectively which is in good agreement with experiment. Inclusion of entropy terms to compute free energy barriers did not change them from the above values, consistent with the small $\Delta S^\dagger$ values experimentally.

The increase and orientation of the dipole in the flat inversion TS suggest that charge may be shifting from the vicinal nitrogen centers into the carbonyl groups of the urazole ring, and perhaps gaining some delocalization and potentially aromatic stabilization for these two formally 4n+2 π electron rings. NICS(1)zz (Nucleus Independent Chemical Shift) calculations were determined on all four rings of the GS and TS structures. NICS(1)zz extracts the out-of-plane (zz) tensor component of the isotropic NICS, thus minimizing σ-orbital contributions. Positive values of ΔNICS(1)zz upon ring flattening would indicate increased paratropic (i.e., antiaromatic) ring current, suggesting destabilization of the TS, and vice versa. The ΔNICS(1)zz values observed for both the 4- and 5-membered rings show substantial paratropic shifts at −3.2 and −4.8 ppm for probe sites positioned 1 Å above the center of the respective rings (exo face, for GS). The implication is that despite improved π overlap and potential for delocalization, aromaticity is not an element in stabilizing the inversion TS.

Based on the puckered nature of the scaffold that is evident in the samples analyzed by X-ray crystallography, and based on the experimental observation of the racemizing inversion by dynamic $^1$H NMR, and our computational results, the diazacyclobutanes studied are not aromatic, even in the TS that is traversed during the inversion process.

Example 4: One-Pot Synthesis of Compound 1

To a flame dried round bottom flask equipped with a stir bar was added a solution of 4-phenylurazole (271 mg, 1.5 mmol) and calcium hypochlorite (429 mg, 3 mmol) in dichloromethane (15 mL). The reaction was stirred at room temperature for 1.5 h. Anhydrous sodium sulfate (426 mg, 3 mmol) was added to the flask and the mixture was stirred for an additional 0.5 h. The suspension was gravity filtered into a clean flask and the resultant mixture was concentrated under reduced pressure to afford a red residue. The residue was transferred with dry dichloromethane (3 mL) to a new flame dried round bottom flask equipped with a stir bar and anhydrous magnesium chloride (14 mg, 0.15 mmol). To this stirring solution was added dropwise a solution of methyl phenylalkynyl sulfide (74 mg, 0.5 mmol) in dry dichloromethane (2 mL). The mixture was stirred at room temperature for 24 h. The resultant mixture was concentrated under reduced pressure and purified via flash chromatography with hexane and ethyl acetate (gradient from 100% hexane to 9:1 hexane/ethyl acetate) to afford the corresponding diazacyclobutene (158 mg, 98% yield).

Characterization of Various Compounds

Compound 1: Light yellow solid; Yield: 89% (288 mg); Mp: 98.6-99.6° C.; IR (neat): 2927 (w), 1784 (m), 1732 (s), 1595 (w), 1384 (s), 1220 (s), 696 (s), 686 (s) cm$^{-1}$; $^1$H-NMR (500 MHz, CDCl$_3$) δ 8.00-7.78 (m, 2H), 7.67-7.31 (m, 8H), 2.59 (s, 3H); $^{13}$C NMR (125 MHz, CDCl$_3$) δ=156.5, 155.1, 145.3, 130.8, 129.9, 129.3, 129.1, 128.8, 126.3, 125.6, 125.4, 17.4; HRMS (ESI$^+$): Calcd for $C_{17}H_{14}N_3O_2S$ [M+H]$^+$ 324.0807 Found m/z 324.0822.

Compound 2: Light yellow solid; Yield: 84% (283 mg); Mp: 90.6-91.2° C.; IR (neat): 3061 (w),2962 (w), 2929 (w), 1793 (m), 1726 (s), 1595 (w), 1386 (s), 1213 (s), 698 (s), 686 (s) cm$^{-1}$; $^1$H-NMR (500 MHz, CDCl$_3$) δ 7.92 (d, J=8.2 Hz, 2H), 7.78-7.29 (m, 8H), 3.06 (q, J=7.2 Hz, 2H), 1.41 (t, J=7.3 Hz, 3H); $^{13}$C NMR (125 MHz, CDCl$_3$) δ=156.3, 155.0, 146.9, 130.8, 129.9, 129.3, 129.1, 128.7, 128.1, 126.3, 125.5, 125.4, 29.2, 15.1; HRMS (ESI⁺): Calcd for C$_{18}$H$_{16}$N$_3$O$_2$S, [M+H]⁺338.0963 Found m/z 338.0980.

Compound 3: Light yellow solid; Yield: 80% (281 mg); Mp: 85.2-86.2° C.; IR (neat): 3068 (w), 2962 (w), 2929 (w), 2870 (w), 1793 (m), 1728 (s), 1593 (w), 1386 (s), 1213 (s), 700 (s), 686 (s) cm⁻¹; ¹H-NMR (500 MHz, CDCl$_3$) δ 8.02-7.80 (m, 2H), 7.64-7.32 (m, 8H), 3.02 (t, J=6.4 Hz, 2H), 1.77 (q, J=7.3 Hz, 2H), 1.05 (t, J=7.3 Hz, 3H); ¹³C NMR (125 MHz, CDCl$_3$) δ=156.4, 155.1, 146.5, 130.9, 129.9, 129.3, 129.1, 128.7, 128.5, 126.4, 125.5, 125.4, 36.8, 23.2, 13.0; HRMS (ESI⁺): Calcd for C$_{19}$H$_{18}$N$_3$O$_2$S, [M+H]⁺ 352.1120 Found m/z 352.1129.

Compound 4: Light yellow solid; Yield: 77% (281 mg); Mp: 60.5-61.7° C.; IR (neat): 3066 (w),2960 (w), 2931 (w), 2872 (w), 2856 (w), 1788 (m), 1728 (s), 1595 (w), 1388 (s), 1217 (s), 698 (s), 684 (s) cm⁻¹; ¹H-NMR (500 MHz, CDCl$_3$) δ 7.88 (d, J=7.5 Hz, 2H) 7.60-7.30 (m, 8H), 3.04 (t, J=7.5 Hz, 2H), 1.72 (p, J=7.3 Hz, 2H), 1.47 (sext, J=7.3 Hz, 2H), 0.92 (t, J=7.3 Hz, 3H); ¹³C NMR (125 MHz, CDCl$_3$) δ=156.4, 155.2, 146.5, 130.9, 129.9, 129.3, 129.1, 128.8, 128.6, 126.4, 125.5, 125.4, 34.6, 31.8, 21.5, 13.5; HRMS (ESI⁺): Calcd for C$_{20}$H$_{20}$N$_3$O$_{2S}$, [M+H]⁺ 366.1276 Found m/z 366.1286.

Compound 5: Light yellow solid; Yield: 78% (296 mg); Mp: 70.7-71.2° C.; IR(neat): 3066 (w), 2953 (w), 2927 (w), 2856 (w), 1791 (m), 1730 (s), 1595 (w), 1388 (s), 1213 (s), 698 (s), 684 (s) cm⁻¹; ¹H-NMR (500 MHz, CDCl$_3$) δ 7.95-7.85 (m, 2H), 7.6-7.3 (m, 8H), 3.03 (t, J=7.3 Hz, 2H), 1.73 (p, J=7.3 Hz, 2H), 1.5-1.2 (m, 4H), 0.87 (t, J=7.1 Hz, 3H); ¹³C NMR (125 MHz, CDCl$_3$) δ=156.3, 155.2, 146.5, 130.9, 129.9, 129.3, 129.1, 128.7, 128.6, 126.4, 125.5, 125.4, 34.9, 30.5, 29.4, 22.1, 13.9; HRMS (ESI⁺): Calcd for C$_{21}$H$_{22}$N$_3$O$_2$S, [M+H]⁺ 380.1433 Found m/z 380.1437.

Compound 6: Light yellow solid; Yield: 81% (341 mg); Mp: 36.3-37.3° C.; IR (neat): 3066 (w), 2924 (m), 2852 (w), 1789 (m), 1732 (s), 1595 (w), 1386 (s), 1215 (s), 700 (s), 686 (s) cm⁻¹; ¹H-NMR (300 MHz, CDCl$_3$) δ 7.89 (d, J=6.6 Hz, 2H), 7.6-7.3 (m, 8H), 3.03 (t, J=7.3 Hz, 2H), 1.73 (p, J=7.4 Hz, 2H), 1.56-1.36 (m, 2H), 1.35-1.15 (broad m, 8H), 0.86 (t, J=6.7 Hz, 3H); ¹³C NMR (75 MHz, CDCl$_3$) δ=156.4, 155.2, 146.5, 130.9, 129.9, 129.3, 129.1, 128.7, 128.6, 126.4, 125.5, 125.4, 34.9, 31.7, 29.8, 29.1, 29.0, 28.4, 22.6, 14.0; HRMS (ESI⁺): Calcd for C$_{24}$H$_{28}$N$_{13}$O$_2$S, [M+H]⁺ 422.1902 Found m/z 422.1909.

Compound 7: Light Pink solid; Yield: 62% (248 mg); Mp: 92.6-93.8° C.; IR (neat): 3061 (w), 3026 (w), 2929 (w), 2850 (w), 1786 (m), 1735 (s), 1595 (w), 1386 (s), 1224 (s), 694 (s), 682 (s) cm⁻¹; ¹H-NMR (300 MHz, CDCl$_3$) δ 7.8-7.1 (m, 15H), 4.21 (s, 2H); ¹³C NMR (75 MHz, CDCl$_3$) δ=156.7, 154.9, 148.6, 136.3, 130.8, 130.1, 129.4, 129.2, 129.1, 128.6, 128.5, 127.8, 127.0, 125.9, 125.5, 125.5, 39.2; HRMS (ESI⁺): Calcd for C$_{23}$H$_{18}$N$_3$O$_2$S, [M+H]⁺ 400.1120 Found m/z 400.1136.

Compound 8: White Solid; Yield: 85% (328 mg); Mp: 171.7-172.7° C.; IR (neat): 2924 (w), 2850 (w), 1789 (m), 1732 (s), 1593 (w), 1577 (w), 1384 (s), 1215 (s), 1149 (s), 1006 (m), 918 (m), 740 (s) 682 (s) cm⁻¹; ¹H-NMR (300 MHz, CDCl$_3$) δ 7.90-7.80 (m, 2H), 7.60-7.40 (m, 10H), 7.40-7.29 (m, 3H); ¹³C NMR (75 MHz, CDCl$_3$) δ=155.6, 154.8, 148.2, 131.8, 130.7, 130.6, 129.7, 129.6, 129.3, 129.1, 128.8, 128.1, 125.9, 125.9, 125.8, 125.4; HRMS (ESI⁺): Calcd for C$_{22}$H$_{16}$N$_3$O$_2$S, [M+H]⁺ 386.0963 Found m/z 386.0978.

Compound 9: White yellow solid; Yield: 92% (310 mg); Mp: 144.7-145.8° C.; IR (neat): 3072 (w), 3034 (w), 2997 (w), 2926 (w), 2850 (s), 1782 (m), 1724 (s), 1595 (w), 1382 (s), 1217 (s), 690 (s)cm⁻¹; ¹H-NMR (300 MHz, CDCl$_3$) δ 7.78 (d, J=8.0 Hz, 2H), 7.6-7.4 (m, 5H), 7.27 (d, J=8.0 Hz, 2H), 2.58 (s, 3H), 2.41 (s, 3H); ¹³C NMR (75 MHz, CDCl$_3$) δ=156.7, 155.1, 145.9, 140.4, 130.9, 129.5, 129.3, 129.1, 128.3, 125.6, 125.4, 123.5, 21.6, 17.5; HRMS (ESI⁺): Calcd for C$_{18}$H$_{16}$N$_3$O$_2$S, [M+H]⁺338.0963 Found m/z 338.0978.

Compound 10: White solid; Yield: 77% (271 mg); Mp: 105.3-106.3° C.; IR (neat): 2966 (w), 2931 (w), 2866 (w), 1782 (m), 1728 (s), 1627 (w), 1597 (w), 1496 (m), 1388 (s), 1226 (s), 1145 (s), 1103 (s), 1018 (m), 921 (m), 875 (m), 813 (m), 767 (s), 686 (s) cm⁻¹; ¹H-NMR (300 MHz, CDCl$_3$) δ 7.80 (d, J=8.2 Hz, 2H), 7.55-7.37 (m, 5H), 7.26 (d, J=8.01 Hz, 2H), 3.03 (q, J=7.3 Hz, 2H), 2.39 (s, 3H), 1.39 (t, J=7.3 Hz, 3H); ¹³C NMR (75 MHz, CDCl$_3$) δ=156.6, 155.1, 147.5, 140.5, 130.8, 129.4, 129.3, 129.1, 127.1, 125.6, 125.4, 123.5, 29.3, 21.6, 15.1; HRMS (ESI⁺): Calcd for C$_{19}$H$_{18}$N$_3$O$_2$S, [M+H]⁺352.1120 Found m/z 352.1130.

Compound 11: White solid; Yield: 74% (262 mg); Mp: 116.1-116.5° C.; IR (neat): 3070 (w), 3014 (w), 2962 (w), 2927 (w), 2837 (w), 1782 (m), 1724 (s), 1602 (m), 1384 (s), 1257 (s), 1226 (m), 688 (s)cm⁻¹; ¹H-NMR (500 MHz, CDCl$_3$) δ 7.94-7.71 (m, 2H), 7.59-7.34 (m, 5H), 7.02-6.90 (m, 2H), 3.84 (s, 3H), 2.54 (s, 3H); ¹³C NMR (125 MHz, CDCl$_3$) δ=160.9, 156.9, 155.2, 145.9, 130.8, 129.2, 129.0, 127.4, 126.9, 125.3, 118.8, 114.2, 55.3, 17.6; HRMS (ESI⁺): Calcd for C$_{18}$H$_{15}$N$_3$O$_3$S, [M+H]⁺354.0912 Found m/z 354.0928.

Compound 12: White solid; Yield: 85% (304 mg); Mp: 135.8-136.9° C.; IR (neat): 3091 (w), 3072 (w), 2926 (w), 1784 (m), 1732 (s), 1593 (w), 1381 (s), 825 (s), 686 (s)cm⁻¹; ¹H-NMR (500 MHz, CDCl$_3$) δ 7.80 (d, J=8.7 Hz, 2H), 7.58-7.36 (m, 7H), 2.59 (s, 3H); ¹³C NMR (125 MHz, CDCl$_3$) δ=156.2, 155.0, 144.0, 135.8, 130.7, 129.8, 129.4, 129.2, 129.1, 126.8, 125.4, 124.8, 17.3; HRMS (ESI⁺): Calcd for C$_{17}$H$_{13}$N$_3$O$_2$SCl, [M+H]⁺ 358.0417 Found m/z 358.0432.

Compound 13: White solid; Yield: 83% (325 mg); Mp: 79.6-81.4° C.; IR (neat): 3068 (w), 3045 (w), 2922 (w), 1788 (m), 1732 (s), 1614 (w), 1388 (s), 1317 (s), 696 (s), 684 (s)cm⁻¹; ¹H-NMR (300 MHz, CDCl$_3$) δ 7.94 (d, J=8.2 Hz, 2H), 7.70 (d, J=8.2 Hz, 2H), 7.60-7.40 (m, 5H), 2.63 (s, 3H); ¹³C NMR (75 MHz, CDCl$_3$) δ=155.8, 155.0, 142.8, 131.8, 131.1 (q, ²J$_{C-F}$=32.9 Hz), 130.7, 129.7 (q, ⁴J$_{C-F}$=1.47 Hz), 129.4, 129.3, 125.8 (q, ³J$_{C-F}$=3.8 Hz), 125.6, 125.4, 123.7 (q, ¹J$_{C-F}$=272.2 Hz), 17.1; HRMS (ESI⁺): Calcd for C$_{18}$H$_{13}$N$_3$O$_2$SF$_3$, [M+H]⁺ 392.0681 Found m/z 392.0693.

Compound 14: White solid; Yield: 61% (185 mg); Mp: 44.8-45.7° C.; IR (neat): 2958 (w), 2927 (w), 2860 (w), 1797 (m), 1739 (s), 1593 (w), 1390 (s), 1211 (m),694 (s) cm⁻¹; ¹H-NMR (300 MHz, CDCl$_3$) δ 7.55-7.35 (m, 5H), 2.54 (t, J=7.5 Hz, 2H), 2.44 (s, 3H), 1.70 (p, J=7.5 Hz, 2H), 1.42 (sext, J=7.4 Hz, 2H), 0.95 (t, J=7.3 Hz, 3H); ¹³C NMR (75 MHz, CDCl$_3$) δ=156.7, 155.1, 150.5, 132.2, 130.9, 129.2, 128.9, 125.2, 28.0, 25.3, 22.1, 17.8, 13.4; HRMS (ESI⁺): Calcd for C$_{15}$H$_{18}$N$_3$O$_2$S, [M+H]⁺304.1120 Found m/z 304.1138.

Compound 15: Colorless liquid; Yield: 56% (193 mg); IR (neat): 2958 (w), 2931 (w), 2870 (w), 1793 (w), 1735 (s), 1597 (w), 1500 (m), 1458 (w), 1377 (s), 1211 (m), 1138 (m), 1072 (m), 999 (m), 921 (m), 748 (m), 690 (m) cm⁻¹; ¹H-NMR (300 MHz, CDCl$_3$) δ 7.60-7.35 (m, 5H), 2.87 (bs, 2H), 2.54 (t, J=7.5 Hz, 2H), 1.80-1.55 (m, 4H), 1.52-1.35 (m, 4H), 1.00-0.85 (m, 6H); ¹³C NMR (75 MHz, CDCl$_3$) δ=156.5, 155.2, 151.7, 131.2, 130.9, 129.3, 128.9, 125.3, 34.2, 31.5, 28.1, 25.3, 22.1, 21.3, 13.5 (2C, See 2D-HMQC analysis); HRMS (ESI⁺): Calcd for C$_{18}$H$_{24}$N$_3$O$_2$S, [M+H]⁺ 346.1589 Found m/z 346.1608.

Compound 16: White solid; Yield: 94% (270 mg); Mp: 71.5-72.5° C.; IR (neat): 2924 (w), 1793 (w), 1739 (s), 1643 (w), 1593 (w), 1492 (m), 1454 (w), 1427 (w), 1388 (s), 1261 (m), 1215 (s), 1149 (s), 1091 (m), 999 (m), 972 (m), 775 (m), 756 (m), 690 (m) cm$^{-1}$; $^1$H-NMR (300 MHz, CDCl$_3$) δ 7.55-7.35 (m, 5H), 2.41 (s, 3H), 1.90-1.60 (m, 1H), 1.40-1.06 (bm, 2H), 1.06-0.90 (bm, 2H); $^{13}$C NMR (75 MHz, CDCl$_3$) δ=156.5, 154.9, 151.2, 130.7, 130.5, 129.1, 128.8, 125.1, 17.8, 6.9, 6.6.

Compound 17: White yellow solid; Yield: 80% (296 mg); Mp: 82.6-83.9° C.; IR (neat): 3066 (w), 3016 (w), 2924 (w), 2850 (w), 1786 (m), 1732 (s), 1631 (w), 1597 (w), 1504 (m), 1489 (m), 1381 (s), 1222 (s), 1141 (s), 1095 (m), 1072 (m), 1018 (s), 758 (m), 744 (m), 682 (s) cm$^{-1}$; $^1$H-NMR (300 MHz, CDCl$_3$) δ 7.94-7.84 (m, 2H), 7.56-7.36 (m, 8H), 2.47 (s, 3H); $^{13}$C NMR (75 MHz, CDCl$_3$) δ=156.3, 154.9, 146.5, 130.8, 129.8, 129.3, 129.1, 128.7, 126.4, 125.3, 125.3, 121.3, 8.7; HRMS (ESI$^+$): Calcd for C$_{17}$H$_{14}$N$_3$O$_2$Se, [M+H]$^+$ 372.0251 Found m/z 372.0269.

Compound 18: White yellow solid; Yield: 93% (402 mg); Mp: 162-162.8° C.; IR (neat): 3070 (w), 2924 (w), 2850 (w), 1793 (m), 1735 (s), 1631 (w), 1593 (w), 1573 (w), 1384 (s), 1276 (m), 1215 (s), 1141 (m), 1107 (m), 1068 (m), 995 (m), 918 (m), 883 (m), 756 (m), 736 (s), 686 (s) cm$^{-1}$; $^1$H-NMR (300 MHz, CDCl$_3$) δ 8.00-7.90 (m, 2H), 7.70-7.60 (m, 2H), 7.53-7.38 (m, 8H), 7.38-7.29 (m, 3H); $^{13}$C NMR (75 MHz, CDCl$_3$) δ=155.7, 154.8, 148.1, 132.2, 130.8, 130.4, 129.8, 129.3, 129.1, 128.8, 128.4, 128.2, 126.1, 125.6, 125.4, 120.7; HRMS (ESI$^+$): Calcd for C$_{22}$H$_{16}$N$_3$O$_2$Se, [M+H]$^+$ 434.0408 Found m/z 434.0417.

The invention has been described with reference to the preferred embodiments without limit thereto. One of skill in the art would realize additional embodiments and improvements which are not specifically stated but which are within the meets and bounds of the claims appended hereto.

The invention claimed is:

1. A compound having the formula:

wherein:
$R^1$ is selected from the group consisting of H, aliphatic of 1 to 100 carbons, arene of up to 100 carbons and a linking group;
each $R^3$ is independently selected from the group consisting of H, aliphatic of 1 to 100 carbons, arene of up to 100 carbons and a linking group;
Y is selected from the group consisting of —(CR$^4{}_A$)$_m$—, —NR$^2$— and —O—;
wherein m is an integer selected from 1 and 2;
A is an integer of 1 or 2,
$R^2$ is selected from the group consisting of H, aliphatic of 1 to 100 carbons, arene of up to 100 carbons and a linking group; and
each $R^4$ is independently selected from the group consisting of H, aliphatic of 1 to 100 carbons, arene of up to 100 carbons and a linking group and combinations thereof;
X is selected from the group consisting of B, O, N, S, Se and P; and
n is 1-4 as necessary to complete the valence of X.

2. The compound of claim 1 wherein said $R^2$ is substituted.

3. The compound of claim 2 wherein said $R^2$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

4. The compound of claim 3 wherein said $R^2$ is substituted with a substituent selected from the group consisting of halogen, alkyl, aryl, hydroxyl, carboxyl and carbonate.

5. The compound of claim 1 wherein each said $R^4$ is independently selected from the group consisting of H, aliphatic of 1 to 100 carbons and arene of up to 100 carbons and combinations thereof, the aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

6. The compound of claim 5 wherein each said $R^4$ is taken together to form an organic ring, a heteroatom ring or an arene.

7. The compound of claim 6 wherein each said $R^4$ is taken together to form a phenyl ring.

8. The compound of claim 1 wherein at least one of said $R^1$ or $R^3$ is substituted.

9. The compound of claim 8 wherein at least one of said $R^1$ or $R^3$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

10. The compound of claim 9 wherein at least one of said $R^1$ or $R^3$ is substituted with a substituent selected from the group consisting of halogen, alkyl, aryl, hydroxyl, carboxyl and carbonate.

11. The compound of claim 1 wherein at least one of said $R^1$, $R^2$, $R^3$ or $R^4$ is a linking group.

12. The compound of claim 11 wherein said linking group is selected from the group consisting of aliphatic, oligomeric glycol, and arene.

13. The compound of claim 1 wherein said X is selected from the group consisting of S, Se, N and O.

14. The compound of claim 13 wherein said X is selected from the group consisting of S and Se.

15. The compound of claim 1 wherein said n is 1 or 2.

16. A compound having the formula:

wherein:
R¹ is selected from the group consisting of H, aliphatic of 1 to 100 carbons and arene of up to 100 carbons;
R² is selected from the group consisting of H, aliphatic of 1 to 100 carbons and arene of up to 100 carbons;
each R³ is independently selected from the group consisting of H, aliphatic of 1 to 100 carbons and arene of up to 100 carbons;
X is selected from the group consisting of B, O, N, S, Se and P; and
n is 1-4 as necessary to complete the valence of X.

17. The compound of claim 16 wherein at least one of said R¹, R² or R³ is substituted.

18. The compound of claim 17 wherein at least one of said R¹, R² or R³ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

19. The compound of claim 18 wherein at least one of said R¹, R² or R³ is substituted with a substituent selected from the group consisting of halogen, alkyl, aryl, hydroxyl, carboxyl and carbonate.

20. The compound of claim 16 wherein said X is selected from the group consisting of S, Se, N and O.

21. The compound of claim 16 wherein said X is selected from the group consisting of S and Se.

22. The compound of claim 16 wherein said n is 1 or 2.

23. The compound of claim 16 wherein at least one of said R¹, R² or R³ or is a linking group.

24. The compound of claim 23 wherein said linking group is selected from the group consisting of aliphatic, oligomeric glycol, and arene.

25. A method for forming a diazacyclobutene derivative comprising the steps of:
forming a first solution comprising a solvent and a compound represented by Formula V:

wherein:
Y is selected from the group consisting of —(CR⁴_A)_m—, —NR²— and —O—;

wherein m is an integer selected from 1 and 2;
A is an integer of 1 or 2;
R² is selected from the group consisting of H, aliphatic, of 1 to 100 carbons, arene of up to 100 carbons and a linking group; and
each R⁴ is independently selected from the group consisting of H, aliphatic of 1 to 100 carbons, arene of up to 100 carbons and a linking group or combinations thereof;
forming a second solution comprising a second solvent and a compound of Formula IV:

wherein:
R¹ is selected from the group consisting of H, aliphatic of 1 to 100 carbons, arene of up to 100 carbons and a linking group;
each R³ is independently selected from the group consisting of H, aliphatic of 1 to 100 carbons, arene of up to 100 carbons, and a linking group;
X is selected from the group consisting of B, O, N, S, Se and P; and
n is 1-4 as necessary to complete the valence of X;
mixing said first solution and said second solution to form a reaction solution; and
heating said reaction solution to a reaction temperature.

26. The method for forming a diazacyclobutene derivative of claim 25 wherein said R² is substituted.

27. The method for forming a diazacyclobutene derivative of claim 26 wherein said R² is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

28. The method for forming a diazacyclobutene derivative of claim 27 wherein said R² is substituted with a substituent selected from the group consisting of halogen, alkyl, aryl, hydroxyl, carboxyl and carbonate.

29. The method for forming a diazacyclobutene derivative of claim 25 wherein each said R⁴ is independently selected from the group consisting of H, aliphatic of 1 to 100 carbons and arene of up to 100 carbons or combinations thereof, the aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

30. The method for forming a diazacyclobutene derivative of claim 29 wherein each said $R^4$ is taken together to form an organic ring, a heteroatom ring or an arene.

31. The method for forming a diazacyclobutene derivative of claim 30 wherein each said $R^4$ is taken together to form a phenyl ring.

32. The method for forming a diazacyclobutene derivative of claim 25 wherein at least one of said $R^1$ or $R^3$ is substituted.

33. The method for forming a diazacyclobutene derivative of claim 32 wherein at least one of said $R^1$ or $R^3$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

34. The method for forming a diazacyclobutene derivative of claim 29 wherein at least one of said $R^1$ or $R^3$ is substituted with a substituent selected from the group consisting of halogen, alkyl, aryl, hydroxyl, carboxyl and carbonate.

35. The method for forming a diazacyclobutene derivative of claim 25 wherein at least one of said $R^1$, $R^2$, $R^3$ or $R^4$ is a linking group.

36. The method for forming a diazacyclobutene derivative of claim 35 wherein said linking group is selected from the group consisting of aliphatic, oligomeric glycol, and arene.

37. The method for forming a diazacyclobutene derivative of claim 25 wherein said X is selected from the group consisting of S, Se, N and O.

38. The method for forming a diazacyclobutene derivative of claim 25 wherein said X is selected from the group consisting of S and Se.

39. The method for forming a diazacyclobutene derivative of claim 25 wherein said n is 1 or 2.

40. The method for forming a diazacyclobutene derivative of claim 25 further comprising adding a Lewis Acid catalyst to said reaction solution.

41. The method for forming a diazacyclobutene derivative of claim 25 wherein said method comprises a one pot synthesis.

42. The method for forming a diazacyclobutene derivative of claim 41 wherein said one pot synthesis comprises forming said Formula V from a urazole.

43. The method for forming a diazacyclobutene derivative of claim 42 wherein said forming said Formula V from said urazole comprises reacting said urazole with calcium hypochlorite.

44. A method for forming a diazacyclobutene derivative comprising the steps of:
forming a first solution comprising a solvent and a compound of Formula III:

Formula III wherein:
$R^2$ is selected from the group consisting of H, aliphatic, of 1 to 100 carbons and arene of up to 100 carbons;
forming a second solution comprising a second solvent and a compound of Formula IV:

Formula IV wherein:
$R^1$ is selected from the group consisting of H, aliphatic of 1 to 100 carbons and arene of up to 100 carbons;
each $R^3$ is independently selected from the group consisting of H, aliphatic of 1 to 100 carbons and arene of up to 100 carbons;
X is selected from the group consisting of B, O, N, S, Se and P; and
n is 1-4 as necessary to complete the valence of X;
mixing said first solution and said second solution to form a reaction solution; and
heating said reaction solution to a reaction temperature.

45. The method for forming a diazacyclobutene derivative of claim 44 wherein said diazacyclobutene derivative is defined by the formula:

46. The method for forming a diazacyclobutene derivative of claim 44 wherein at least one of said $R^1$, $R^2$ or $R^3$ is substituted.

47. The method for forming a diazacyclobutene derivative of claim 46 wherein at least one of said $R^1$, $R^2$ or $R^3$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

48. The method for forming a diazacyclobutene derivative of claim 47 wherein at least one of said $R^1$, $R^2$ or $R^3$ is substituted with a substituent selected from the group consisting of halogen, alkyl, aryl, hydroxyl, carboxyl and carbonate.

49. The method for forming a diazacyclobutene derivative of claim 44 wherein said X is selected from the group consisting of S, Se, N and O.

50. The method for forming a diazacyclobutene derivative of claim 44 wherein said X is selected from the group consisting of S and Se.

51. The method for forming a diazacyclobutene derivative of claim 44 wherein said n is 1 or 2.

52. The method for forming a diazacyclobutene derivative of claim 44 wherein said first solvent and said second solvent are the same.

53. The method for forming a diazacyclobutene derivative of claim 44 wherein at least one of said first solvent or said second solvent is selected from the group consisting of tetrahydrofuran, acetonitrile, dichloromethane, toluene and chloroform.

54. The method for forming a diazacyclobutene derivative of claim 44 wherein said reaction temperature is at least 25° C. to no more than 300° C.

55. The method for forming a diazacyclobutene derivative of claim 54 wherein said reaction temperature is at least 50° C. to no more than 250° C.

56. The method for forming a diazacyclobutene derivative of claim 54 wherein said reaction temperature is at least 100° C. to no more than 200° C.

57. The method for forming a diazacyclobutene derivative of claim 44 wherein said mixing is for at least 6 hours to no more than 24 hours.

58. The method for forming a diazacyclobutene derivative of claim 44 further comprising adding a Lewis Acid catalyst to said reaction solution.

59. The method for forming a diazacyclobutene derivative of claim 44 wherein at least one of said $R^1$, $R^2$ or $R^3$ is a linking group.

60. The method for forming a diazacyclobutene derivative of claim 59 wherein said linking group is selected from the group consisting of aliphatic, oligomeric glycol, and arene.

61. The method for forming a diazacyclobutene derivative of claim 44 wherein said method comprises a one pot synthesis.

62. The method for forming a diazacyclobutene derivative of claim 61 wherein said one pot synthesis comprises forming said Formula III from a urazole.

63. The method for forming a diazacyclobutene derivative of claim 62 wherein said forming said Formula III from said urazole comprises reacting said urazole with calcium hypochlorite.

* * * * *